United States Patent [19]

Cook et al.

[11] Patent Number: 5,554,646
[45] Date of Patent: Sep. 10, 1996

[54] METHOD FOR REDUCING BODY FAT IN ANIMALS

[75] Inventors: Mark E. Cook; Michael W. Pariza; Yeonhwa Park, all of Madison, Wis.

[73] Assignee: Wisconsin Alumni Research Foundation, Madison, Wis.

[21] Appl. No.: 297,472

[22] Filed: Aug. 29, 1994

Related U.S. Application Data

[63] Continuation-in-part of Ser. No. 875,896, Apr. 29, 1992, Pat. No. 5,430,066, which is a continuation-in-part of Ser. No. 7,413, Jan. 22, 1993, Pat. No. 5,428,072.

[51] Int. Cl.$^6$ .................... A61K 31/20; A61K 31/23
[52] U.S. Cl. ............................ 514/560; 514/549
[58] Field of Search ........................ 514/560, 549

[56] References Cited

U.S. PATENT DOCUMENTS

| | | | |
|---|---|---|---|
| 4,282,265 | 8/1981 | Theuer | 426/607 |
| 4,603,142 | 7/1986 | Burger et al. | 514/456 |
| 4,868,001 | 9/1989 | Maruta | 426/623 |
| 5,017,614 | 5/1991 | Pariza et al. | 514/558 |
| 5,070,104 | 12/1991 | Pariza et al. | 514/549 |
| 5,162,337 | 11/1992 | Elbrecht et al. | 514/300 |
| 5,428,072 | 6/1995 | Cook et al. | 514/560 |
| 5,443,844 | 8/1995 | McDaniel | 424/484 |
| 5,484,623 | 1/1996 | McLean | 426/601 |

FOREIGN PATENT DOCUMENTS

| | | |
|---|---|---|
| 0376628A3 | 4/1990 | European Pat. Off. . |
| 0579901A1 | 1/1994 | European Pat. Off. . |
| 294982 | 9/1986 | Japan . |
| WO9201450 | 6/1992 | WIPO . |
| WO9416690 | 4/1994 | WIPO . |

OTHER PUBLICATIONS

Miller, Park, Pariza, Cook–"Feeding Conjugated Linoleic Acid to Animals Partially Overcomes Catabolic Responses Due to Endotoxin Injection", Feb. 15, 1994, vol. 198, No. 3, 1994 Biochemical Research Communications, pp. 1107–1112.

Chin, Storkson, Liu, Albright, Pariza, "Conjugated Linoleic Acid...", Nutrient Metabolism, Univ. of Wisconsin–Madison, May 1994, pp. 694–701.

Chin, Storkson, Pariza; "Conjugated Dienoic Derivatives of Linoleic Acid", Chapter 21, 1993 Am. Chemical Society.

Fogerty, Ford and Svoronos; "Dienoic Acid in Foodstuffs and in the Lipids of Human Blood and Breast Milk," Nutrition Reports Intl., Nov. 1988, vol. 38, No. 5.

Y. L. Ha; N. K. Grimm and M. W. Pariza, *Carcinogenesis*, vol. 8, No. 12, pp. 1881–1887 (1987).

Y. L. Ha; N. K. Grimm and M. W. Pariza, J. Agric. Food Chem., vol. 37, No. 1, pp. 75–81 (1987).

M. W. Pariza, Food Research Institute 1988 Annual Fall Meeting, Oct. 12, 1988.

The Merck Index, Tenth Edition (1983), p. 790.

The Marck Veterinary Manual, Fifth Edition (1979), pp. 1340–1343 and 1374 to 1379.

Primary Examiner—Jose G. Dees
Assistant Examiner—Barbara S. Frazier
Attorney, Agent, or Firm—Quarles & Brady

[57] ABSTRACT

A method of reducing body fat comprises administering to the animal a safe and effective amount of a conjugated linoleic acid. Methods of preserving or increasing the animal's body protein by administering the conjugated linoleic acid also are disclosed.

9 Claims, No Drawings

METHOD FOR REDUCING BODY FAT IN ANIMALS

RELATED CASE

The present application is a continuation-in-part of applications U.S. Ser. No. 07/875,896, filed Apr. 29, 1992, now U.S. Pat. No. 5,430,066, and U.S. Serial No. 08/007,413, filed Jan. 22, 1993, now U.S. Pat. No. 5,428,072.

FIELD OF THE INVENTION

The present invention generally relates to animal nutrition. More particularly, it relates to a method of reducing body fat in an animal.

BACKGROUND OF THE INVENTION

In today's health conscious society there is a great interest in the fat content of food. There is a special concern about the saturated fat content of meat because of its alleged relationship to blood cholesterol. As a result, most consumers would prefer to have meats of lower total and saturated fat content. As a result some meats, such as duck and beef, are declining in popularity.

There is an obvious need for a safe and effective method of reducing the body fat of animals, especially meat animals.

There also is a great interest in dieting and other means of controlling the body fat of humans. There also is a need for preventing the loss of body protein in humans such as for example can occur when they are under attack of cytokines, such as tissue necrosis factor (TNF).

As a result there also is a need for both a safe and an effective method for reducing the body fat of humans, and a need for a safe and an effective method of preventing the loss of body protein in humans.

BRIEF SUMMARY OF THE INVENTION

It is an object of the present invention to disclose a method of reducing body fat in an animal.

It is a further object to disclose a method of increasing body protein or preventing the loss of body protein in humans.

We have discovered a method of reducing body fat in an animal which comprises administering to said animal a safe amount of a compound selected from 9,11-octadecadienoic acid; 10,12-octadecadienoic acid; mixtures thereof; and non-toxic salts thereof (CLA), which is effective to reduce body fat. Our method is effective in reducing body fat in both mammals and avian species.

We also have discovered a method of increasing body protein or preventing the loss of body protein in a human which comprises administering to said animal a safe amount of a conjugated linoleic acid selected from 9,11-octadecadienoic acid; 10,12-octadecadienoic acid; mixtures thereof; and non-toxic salts thereof, which is effective to increase and/or prevent the loss of body protein.

It will be apparent to those skilled in the art that the forementioned objects and other advantages may be achieved by the practice of the present invention.

DESCRIPTION OF THE PREFERRED EMBODIMENT

In one preferred embodiment of the method of the present invention the safe and effective amount of conjugated linoleic acid, which is selected from 9,11-octadecadienoic acid; 10,12-octadecadienoic acid; mixtures thereof; and non-toxic salts thereof, is added to the feed of an animal in which it is desired to reduce the body fat. The amount of the conjugated linoleic acid to be added to the animal's feed will vary with the species and size of the animal. However, since the conjugated linoleic acids are natural food ingredients and relatively non-toxic, the amount which can be administered is not critical as long as it is enough to be effective.

The practice of the present invention is further illustrated by the examples which follow:

EXAMPLE 1

SYNTHESIS OF CONJUGATED LINOLEIC ACIDS (CLA) FROM LINOLEIC ACID AND SAFFLOWER OIL

Ethylene glycol (1000 g) and 500 g potassium hydroxide (KOH) are put into a 4-neck round bottom flask (5000 ml). The flask is equipped with a mechanical stirrer, a thermometer, a reflux condenser, and a nitrogen inlet. (The nitrogen introduced in first run through two oxygen traps).

Nitrogen is bubbled into the ethylene glycol and KOH mixture for 20 min and the temperature is then raised to 180° C.

1000 g of linoleic acid, corn oil, or safflower oil is then introduced into the flask. The mixture is heated at 180° C. under an inert atmosphere for 2.5 hours.

The reaction mixture is cooled to ambient conditions and 600 ml HCl is added to the mixture which is stirred for 15 min. The pH of the mixture is adjusted to pH 3. Next, 200 ml of water is added into the mixture and stirred for 5 min. The mixture is transferred into a 4 L separatory funnel and extracted three times with 500-ml portions of hexane.

The aqueous layer is drained and the combined hexane solution extracted with four 250-ml portions of 5% NaCl solution.

The hexane is washed 3 times with water. The hexane is transferred to a flask and the moisture in the hexane removed with anhydrous sodium sulfate ($Na_2SO_4$). The hexane is filtered through Whatman paper into a clean 1000 ml round bottom flask and the hexane removed under vacuum with a rotoevaporator to obtain the CLA. The CLA is stored in a dark bottle under argon at –80° C. until time of use.

EXAMPLE 2

Eight pigs (5 kg. body weight) are fed a standard control diet containing 0.5% corn oil and an equal number are fed the identical diet in which 0.5% of the corn oil is replaced by 0.5% CLA. Diet is provided free choice every day until the pigs are 15 kg. in weight. After the feeding period the pigs are sacrificed and the fat, protein, water and ash content of the carcasses is analyzed. It is found that the carcasses of the pigs fed the CLA diet contain less fat than the pigs fed the control diet.

EXAMPLE 3

The percentage of body fat of male humans, 20 to 45 years old, weighing approximately 10% over their recommended body weight, is determined by the method of body density by hydrostatic weighing. The humans are permitted to eat their usual diet to which 0.1 to 10 grams of CLA has been provided as a food supplement. After 4 to 10 weeks, the percentage of the body fat of the humans is again determined and it is found that the change in the percentage of body fat is reduced.

EXAMPLE 4

Thirty-two mice were fed either a control (5.5% Corn Oil) or a CLA (5% Corn Oil and 0.5% CLA) containing diet for 28 days. Fresh diet were provided every day. Animals were injected intraperitoneally with TNF-α (200 µg/kg body weight) or PBS (phosphate buffered saline). After 28 days the mice were sacrificed and the fat, protein, water and ash content of the carcasses analyzed.

TABLE 1

Body Composition of Mice Fed
0.5% CLA Containing Diet for 28 days.[1]

|  | Control | | CLA | |
| --- | --- | --- | --- | --- |
|  | PBS | TNF-α | PBS | TNF-α |
| ECW (g)[2] | 32.4 ± 1.1 | 31.9 ± 0.8 | 32.2 ± 0.8 | 31.6 ± 0.9 |
| % Water | 66.29 ± 0.78 | 66.61 ± 0.74 | 70.88 ± 0.38 | 71.19 ± 0.40 |
| % Protein | 17.76 ± 0.30 | 17.59 ± 0.23 | 18.58 ± 0.14 | 19.16 ± 0.06 |
| % Fat | 10.13 ± 1.17 | 9.36 ± 0.71 | 4.34 ± 0.40 | 3.66 ± 0.39 |
| % Ash | 3.08 ± 0.14 | 3.11 ± 0.04 | 3.24 ± 0.05 | 3.36 ± 0.04 |

[1]Numbers are mean ± S.E. of 7–8 mice per group.
[2]ECW: Empty Carcass Weight.

The results of the test show that although the overall weight of the control mice and the test mice was about the same, the total fat content of the test mice was significantly lower than that of the control mice. In addition, the percent of protein in the test mice injected with TNF-α was higher than in the control mice.

The average body composition of the control and test mice (CLA) is shown in Table 2.

TABLE 2

Body Composition of Mice Fed
0.5% CLA Containing Diet for 28 days.[1,2]

|  | Control | CLA |
| --- | --- | --- |
| ECW (g)[3] | 32.1 ± 0.6 | 31.9 ± 0.6 |
| % Water | 66.46 ± 0.54 | 71.03 ± 0.28 |
| % Protein | 17.67 ± 0.19 | 18.87 ± 0.10 |
| % Fat | 9.72 ± 0.67 | 4.00 ± 0.29 |
| % Ash | 3.10 ± 0.03 | 3.30 ± 0.03 |

[1]Mice were fed either control (5.5% Corn Oil) or CLA (5% Corn Oil and 0.5% CLA) containing diet for 28 days. Fresh diet were provided every day. Animals were injected intraperitoneally with TNF-α (200 µg/kg body weight) or PBS (phosphate buffered saline).
[2]Numbers are mean ± S.E. of 15–16 mice per group.
[3]ECW: Empty Carcass Weight.

In another embodiment of the invention, free linoleic acid is administered to an animal which can convert the linoleic acid into CLA or which modulates the level of CLA in the body of an animal or a human. The linoleic acid is converted to CLA in the animal, probably by microorganisms in the animal's gastrointestinal system (S. F. Chin, J. M. Storkson, W. Liu, K. Albright, and M. W. Pariza, 1994, J. Nutr. 124: 694–701.

The method of the present invention may take other forms. For example, the CLA can be administered to an animal in a pharmaceutical or veterinary composition, such as tablets, capsules, solutions or emulsions, containing safe and effective doses of the CLA.

The animal feeds and pharmaceutical or veterinary compositions for use in the method of the present invention are those containing the active forms of the free conjugated linoleic acids (CLA), especially 9,11-octadecadienoic acid and 10,12-octadecadienoic acid or mixtures thereof in combination with a conventional animal feed, human food supplement, or an approved pharmaceutical diluent.

The active forms of CLA include, in addition to the free acids the active isomers of CLA; non-toxic salts thereof; active esters and other active chemical derivatives thereof; and mixtures thereof.

The free conjugated linoleic acids (CLA) have been previously isolated from fried meats and described as anti-carcinogens by Y. L. Ha, N. K. Grimm and M. W. Pariza, in Carcinogenesis Vol. 8, No. 12, pp. 1881–1887 (1987). Since then, they have been found in some processed cheese products. Y. L. Ha, N. K. Grimm and M. W. Pariza, in J. Agric. Food Chem., Vol. 37, No. 1, pp. 75–81 (1987). However, animal feeds containing CLA, or its non-toxic derivatives, such as the sodium and potassium salts, as an additive in combination with conventional animal feeds or human foods are believed to be novel.

The free acid forms of the CLA may be prepared by isomerizing linoleic acid. The terms "conjugated linoleic acids" and "CLA" as used herein are intended to include 9,11-octadecadienoic acid, 10,12-octadecadienoic acid, mixtures thereof and the non-toxic salts of the acids. The non-toxic salts of the free acids may be made by reacting the free acids with a non-toxic base.

The preferred method of synthesizing CLA is that described in Example 1. However, CLA may also be prepared from linoleic acid by the action of a linoleic acid isomerase from a harmless microorganism, such as the Rumen bacterium *Butyrivibrio fibrisolvens*. Harmless microorganisms in the intestinal tracts of rats and other monogastric animals may also convert linoleic acid to CLA (S. F. Chin, J. M. Storkson, W. Liu, K. Albright and M. W. Pariza, 1994, J. Nutr. 124; 694-701.

The CLA obtained by the practice of the described methods of preparation contains one or more of the 9,11-octadecadienoic acids and/or 10,12-octadecadienoic acids and active isomers thereof. It may be free or bound chemically through ester linkages. The CLA is heat stable and can be used as is, or dried and powdered. The CLA is readily converted into a non-toxic salt, such as the sodium or potassium salt, by reacting chemically equivalent amounts of the free acid with an alkali hydroxide at a pH of about 8 to 9.

Theoretically, 8 possible geometric isomers of 9,11 and 10,12-octadecadienoic acid (c9,c11; c9,t11; t9,c11; t9,t11; c10,c12; c10,t12; t10,c12 and t10,t12) would form from the isomerization of c9,c12-octadecadienoic acid. As a result of the isomerization, only four isomers (c9,c11; c9,t11; t10, c12; and c10,c12) would be expected. However, of the four isomers, c9,t11- and t10,c12- isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9,t11- or t10,c12-geometric isomers, which is thermodynamically preferred, during an extended processing time or long aging period. Additionally the t,t-isomer of 9,11- or 10,12-octadecadienoic acid that was predominantly formed during the isomerization of linoleic acid geometrical isomers (t9,t12-, c9,t12- and t9,c12-octadecadienoic acid) may influence the final ratio of the isomers or the final CLA content in the samples.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

The exact amount of CLA to be administered, of course, depends upon the animal, the form of CLA employed, and the route of administration. However, generally it will be an amount ranging from about 0.001 g/kg about 1 g/kg of the animals body weight.

Generally, the amount employed of CLA employed as a pharmaceutical for humans will range from about 1,000 parts per million (ppm) to about 10,000 ppm of CLA of the human's diet. However, the upper limit of the amount to be employed is not critical because CLA is relatively non-toxic and it is a normal constituent of the human diet (including human breast milk).

The preferred pharmaceutical and veterinary compositions of CLA contain the non-toxic sodium or potassium salt of CLA in combination with a pharmaceutical diluent. When the compositions are solutions or suspensions intended for oral administration the diluent will be one or more diluents, such as lactose or starch, and the product will be a tablet, capsule or liquid. When the compositions are solutions or suspensions intended for parenteral administration the preferred diluent will be Sterile Water for Injection U.S.P.

The amount of CLA to be added to an animal's feed to reduce body fat can range from 0.01% to 2.0% or more by weight of the animal's or human's food. It can be added to the food by adding either relatively pure CLA to the food or by adding by-products, such as the fat of an animal which was fed CLA, to the food.

An especially preferred composition for use in humans might be a water in oil fat emulsion, such as Intralipid® (Baxter); Liposyn® (Abbott); Nutrilipid® (McGaw); or SoyaCal® (Alpha Therapeutic), in which about 0.5% to about 2% (preferably 1%) by weight of the oil has been replaced by CLA. These fat emulsions all contain emulsified fat particles of about 0.33–0.5 μm in diameter. In addition about 10% to 20% of the oils which are a mixture of neutral triglycerides of principally unsaturated fatty acids, the emulsions contain Water for Injection USP as a diluent, egg phosphatides (1–2%) as an emulsifying agent and glycerin (2–3%) to adjust toxicity. These emulsions can be infused intravenously to patients requiring parenteral nutrition.

Another preferred composition is a baby formula, in which about 0.5% to about 2% by weight (preferably 0.5%) by weight of the fat content has been replaced by a like amount of CLA or to which 0.5% to about 2% by weight has been added.

It will be readily apparent to those skilled in the art that a number of modifications or changes may be made without departing from the spirit and scope of the present invention. Therefore, the invention is only to be limited by the claims.

We claim:

1. A method of reducing body fat in an animal in which it is desired to reduce the body fat which comprises administering to the animal a safe amount of a member selected from the class consisting of a conjugated linoleic acid, a non-toxic salt thereof, an active ester thereof, and mixtures thereof, which is effective to reduce the body fat of the animal.

2. The method of claim 1 in which the amount of conjugated linoleic acid administered is about 0.001 g/kg to about 1 g/kg of the animal's body weight.

3. A method of preserving body protein in an animal in which it desired to preserve body protein which comprises administering to said animal a safe amount of a member selected from the class consisting of a conjugated linoleic acid, a non-toxic salt thereof, an active ester thereof, and mixtures thereof, which is effective to preserve body protein.

4. A method of increasing muscle protein in an animal in which it is desired to increase muscle protein which comprises administering to the animal a safe amount of a member selected from the class consisting of a conjugated linoleic acid, a non-toxic salt thereof, an active ester thereof, and mixtures thereof which is effective to increase muscle protein.

5. A method of claim 4 in which the animal is a mammal.

6. A method of claim 4 in which the animal is an avian species.

7. The method of claim 1 in which the conjugated linoleic acid is administered as the free acid.

8. The method of claim 3 in which the conjugated linoleic acid is administered as the free acid.

9. The method of claim 4 in which the conjugated linoleic acid is administered as the free acid.

* * * * *